(12) United States Patent
Lee et al.

(10) Patent No.: US 7,241,594 B2
(45) Date of Patent: Jul. 10, 2007

(54) GENE ENCODING FORMATE DEHYDROGENASES D & E AND METHOD FOR PREPARING SUCCINIC ACID USING THE SAME

(75) Inventors: Sang Yup Lee, Daejeon (KR); Hyohak Song, Daejeon (KR); Yu Sin Jang, Daejeon (KR); Sung Won Lim, Seoul (KR)

(73) Assignee: Korea Advanced Institute of Science and Technology (KR)

( * ) Notice: Subject to any disclaimer, the term of this patent is extended or adjusted under 35 U.S.C. 154(b) by 0 days.

(21) Appl. No.: 11/228,945

(22) Filed: Sep. 16, 2005

(65) Prior Publication Data

US 2007/0042481 A1 Feb. 22, 2007

(30) Foreign Application Priority Data

Aug. 19, 2005 (KR) .................. 10-2005-0076348

(51) Int. Cl.
*C12P 1/00* (2006.01)
*C12P 21/04* (2006.01)

(52) U.S. Cl. .................. 435/71.2; 435/41; 435/45; 435/71.1

(58) Field of Classification Search ................ None
See application file for complete search history.

(56) References Cited

U.S. PATENT DOCUMENTS

| 5,143,834 A | 9/1992 | Glassner et al. |
| 5,168,055 A | 12/1992 | Datta et al. |
| 5,504,004 A | 4/1996 | Guettler et al. |
| 5,521,075 A | 5/1996 | Guettler et al. |
| 5,770,435 A | 6/1998 | Donnelly et al. |

FOREIGN PATENT DOCUMENTS

WO  WO 2005/052135 A1  6/2005
WO  WO-2005/052135 A1  6/2005

OTHER PUBLICATIONS

STIC Search Report "us-11-228-945-7.rup". p. 1.*
STIC Search Report "us-11-228-945-8.rup". pp. 1-2.*
Lee et al., Metabolic engineering of *Escherichia coli* for enhanced production of succinic acid, based on genome comparison and in silico gene knockout simulation. Appl Environ Microbiol. Dec. 2005;71(12):7880-7.*
Popov et al., NAD(+)-dependent formate dehydrogenase.Biochem J. Aug. 1, 1994;301 ( Pt 3):625-43. Review. No abstract available. Erratum in: Biochem J Sep. 15, 1994;302(Pt 3):967.*
Berrios-Rivera SJ, Bennett GN, San KY.Metabolic engineering of *Escherichia coli*: increase of NADH availability by overexpressing an NAD(+)-dependent formate dehydrogenase. Metab Eng. Jul. 2002;4(3):217-29.*
Chatterjee, Ranjini, et al., Mutation of the ptsG Gene Results in Increased Production of Succinate in Fermentation of Glucose by *Escherichia coli*, Appl. Environ. Microbiol., Jan. 2001, pp. 148-154, vol. 67, No. 1.
Donnelly, Mark I., et al., A novel fermentation pathway in an *Eschorichia coli* mutant producing succinic acid, acetic acid, and ethanol, App. Biochem. Biotech., 1998, pp. 187-198, vol. 70-72.
Zeikus et al., *Appl. Microbiol. Biotechnol.*, 51:545, 1999.
Willke et al., *Appl. Microbiol. Biotechnol.*, 66:131, 2004.
Hong et al., *Biotechnol. Lett.*, 22:871, 2000.
Laivenieks et al., *Appl. Environ. Microbiol.*, 63:2273, 1997.
Hong et al., *Nature Biotechnol.*, 22:1275, 2004.
Kehrenberg et al., *J. Antimicrob. Chemother.*, 49:383, 2002.
Gray et al., *Biochim. Biophys. Acta*, 117:33, 1966.

* cited by examiner

*Primary Examiner*—Joseph Woitach
*Assistant Examiner*—Maria Leavitt
(74) *Attorney, Agent, or Firm*—Steven J. Hultquist; Intellectual Property/Technology Law; Kelly K. Reynolds (57) ABSTRACT

Nucleotide sequences encoding formate dehydrogenases D & E and a method for preparing succinic acid using the same, more particularly, formate dehydrogenases D & E converting formate to carbon dioxide and hydrogen, fdhD and fdhE nucleotide sequences encoding the formate dehydrogenases D & E, recombinant vectors containing the nucleotide sequences, microorganisms transformed with the recombinant vectors, and a method for preparing succinic acid using the transformed microorganism.

15 Claims, 3 Drawing Sheets

SEQUENCE LISTING

<160> NUMBER OF SEQ ID NOS: 8

<210> SEQ ID NO 1
<211> LENGTH: 29
<212> TYPE: DNA
<213> ORGANISM: Artificial Sequence
<220> FEATURE:
<223> OTHER INFORMATION: Synthetic Construct

<400> SEQUENCE: 1
cgggatcctt cttcttgtga cctgcatag                              29

<210> SEQ ID NO 2
<211> LENGTH: 28
<212> TYPE: DNA
<213> ORGANISM: Artificial Sequence
<220> FEATURE:
<223> OTHER INFORMATION: Synthetic Construct

<400> SEQUENCE: 2
cgggatcccg gaagtgcaaa actgtttg                               28

<210> SEQ ID NO 3
<211> LENGTH: 31
<212> TYPE: DNA
<213> ORGANISM: Artificial Sequence
<220> FEATURE:
<223> OTHER INFORMATION: Synthetic Construct

<400> SEQUENCE: 3
ccggaattca tggattgctg cgtaaaactt c                           31

<210> SEQ ID NO 4
<211> LENGTH: 31
<212> TYPE: DNA
<213> ORGANISM: Artificial Sequence
<220> FEATURE:
<223> OTHER INFORMATION: Synthetic Construct

<400> SEQUENCE: 4
ccggaattca gaacaaatgc tgcaatactg g                           31

<210> SEQ ID NO 5
<211> LENGTH: 846
<212> TYPE: DNA
<213> ORGANISM: Mannheimia succiniciproducens MBEL55E

<400> SEQUENCE: 5

| | | | | | |
|---|---|---|---|---|---|
| ttgattgaga | tcacaaaaag | aacaataagt | tttttcaaaa | atttaacatt | tataaaacaa | 60 |
| atagataaag | atacagtatc | agattcaaac | aatagccgtt | ttgaatttat | acaaaaagaa | 120 |
| gaaacgttgg | cggtggaaat | gcccgtagcg | cttgtttata | acggcatttc | tcatacggtg | 180 |
| atgatggcaa | ctccttcaaa | tttggaagat | ttcgctctag | gattttcact | ggcggaaggt | 240 |
| gttatcgata | gagtttcgga | tatttacggc | attgacgttg | aagaaacctg | taacggggta | 300 |
| gaagtgcagg | tggagttggc | aacccgatgt | tttgtccgct | tgaaagattt | acgccgaacc | 360 |
| ttaacgggca | gaacgggttg | tggtatttgc | ggcagcgagc | aacttgaaca | ggtcacaaaa | 420 |
| aaattagcaa | aattagaccg | cacttttgc | tttgaactga | aaaaattaga | cggctgttta | 480 |
| gctctattac | agcaagcgca | gacgttgggt | aagcaaacgg | gttcaaccca | tgcggtaggt | 540 |
| tttttctcgc | cgcaagggga | attgttagca | attcggaag | atgtggggcg | ccatgtggcg | 600 |
| ttagataaat | tattaggctg | gcatgccaag | caaggaaaac | ctcaaggttt | tgttttaact | 660 |
| acaagtcgtg | caagttatga | aatggtgcaa | aaaccgcaa | gttgcgggat | tgaaatgtta | 720 |
| atagccattt | ctgcggcaac | ggatttggcg | gtacgtatgg | cggaagaatg | taatctcact | 780 |
| cttatcggtt | ttgccagaga | gggaagagcg | acggtttaca | ctgaaaaagt | gcggttaaaa | 840 |
| atttag | | | | | | 846 |

<210> SEQ ID NO 6
<211> LENGTH: 984
<212> TYPE: DNA
<213> ORGANISM: Mannheimia succiniciproducens MBEL55E

<400> SEQUENCE: 6

| | | | | | |
|---|---|---|---|---|---|
| atgcaaagca | gccaaaagtg | cggtaaaatt | taccgcactt | ttctattagg | aattataact | 60 |
| atgagtattc | gaatccttcc | ggagcatgaa | atcaaaaaaa | cagcgaccag | ttttgaacaa | 120 |
| ccagcactgc | ttttcgccaa | tcctcagaat | ttatatgagc | gccgggcaaa | gcgtttgcga | 180 |
| aaacttagtg | aatctcatcc | attcgcggaa | tatttgaact | tcgcggcgga | agtttcggaa | 240 |
| gtgcaattaa | agatcttaaa | aatgcacccca | ttgccacaag | acgaacgttt | aacaaaagaa | 300 |
| aatttcagtt | tagataattc | aattcaacct | ttgcatacta | aaaattggaa | acgagatgtt | 360 |
| atttggcgag | aatatctcgc | tgaaaatttta | gcacaaaatca | aacttaaagc | gacaaatcaa | 420 |
| ataacaacaa | ccattgattg | gttagaaaag | gcctcgagata | cagaaattga | atctcttgcc | 480 |
| gataaacttt | tagcagaaga | ttttttcttcg | gtaagcagtg | ataaagctgt | ttttatttgg | 540 |
| gcggctcttt | cgctttactg | gctacaactt | gctcaacaaa | ttcctcatac | gacaaatatg | 600 |
| gaaagcggtg | agaatcttca | cgtttgtccg | gtatgtaatg | cggcaccggt | ggcgagtgtc | 660 |
| gtacattttg | gcgcagctca | aggcttgcgt | tatctgcatt | gttccctctg | tgaaagcgaa | 720 |
| tggaatatgg | ttcgcgccaa | atgtagcaat | tgcaaccaag | ctgaacattt | agaatattgg | 780 |
| tctattgatg | aagaaatggc | ggcagtacga | tccgaaagtt | gcggtgattg | ccattcctac | 840 |
| cttaaaatac | tgttccagga | aaaggatcct | catgttgaac | ctgtagctga | cgatctggca | 900 |
| actatttatc | ttgatataga | gatggaagaa | aaaggttttg | cccgcagcgg | attaaatccc | 960 |
| tttatgttcc | cctcggaaga | agcg | | | | 984 |

<210> SEQ ID NO 7
<211> LENGTH: 281
<212> TYPE: PRT
<213> ORGANISM: Mannheimia succiniciproducens MBEL55E

<400> SEQUENCE: 7

```
Met Ile Glu Ile Thr Lys Arg Thr Ile Ser Phe Phe Lys Asn Leu Thr
1               5                   10                  15

Phe Ile Lys Gln Ile Asp Lys Asp Thr Val Ser Asp Ser Asn Asn Ser
            20                  25                  30

Arg Phe Glu Phe Ile Gln Lys Glu Thr Leu Ala Val Glu Met Pro
        35                  40                  45

Val Ala Leu Val Tyr Asn Gly Ile Ser His Thr Val Met Met Ala Thr
    50                  55                  60

Pro Ser Asn Leu Glu Asp Phe Ala Leu Gly Phe Ser Leu Ala Glu Gly
65                  70                  75                  80

Val Ile Asp Arg Val Ser Asp Ile Tyr Gly Ile Asp Val Glu Glu Thr
                85                  90                  95

Cys Asn Gly Val Glu Val Gln Val Glu Leu Ala Thr Arg Cys Phe Val
            100                 105                 110

Arg Leu Lys Asp Leu Arg Arg Thr Leu Thr Gly Arg Thr Gly Cys Gly
        115                 120                 125

Ile Cys Gly Ser Glu Gln Leu Glu Gln Val Thr Lys Lys Leu Ala Lys
130                 135                 140

Leu Asp Arg Thr Phe Cys Phe Glu Leu Lys Lys Leu Asp Gly Cys Leu
145                 150                 155                 160

Ala Leu Leu Gln Gln Ala Gln Thr Leu Gly Lys Gln Thr Gly Ser Thr
                165                 170                 175

His Ala Val Gly Phe Phe Ser Pro Gln Gly Glu Leu Leu Ala Ile Arg
            180                 185                 190

Glu Asp Val Gly Arg His Val Ala Leu Asp Lys Leu Leu Gly Trp His
        195                 200                 205

Ala Lys Gln Gly Lys Pro Gln Gly Phe Val Leu Thr Thr Ser Arg Ala
    210                 215                 220

Ser Tyr Glu Met Val Gln Lys Thr Ala Ser Cys Gly Ile Glu Met Leu
225                 230                 235                 240

Ile Ala Ile Ser Ala Ala Thr Asp Leu Ala Val Arg Met Ala Glu Glu
                245                 250                 255

Cys Asn Leu Thr Leu Ile Gly Phe Ala Arg Glu Gly Arg Ala Thr Val
            260                 265                 270

Tyr Thr Glu Lys Val Arg Leu Lys Ile
        275                 280
```

<210> SEQ ID NO 8
<211> LENGTH: 328
<212> TYPE: PRT
<213> ORGANISM: Mannheimia succiniciproducens MBEL55E

<400> SEQUENCE: 8

```
Met Gln Ser Ser Gln Lys Cys Gly Lys Ile Tyr Arg Thr Phe Leu Leu
1               5                   10                  15

Gly Ile Ile Thr Met Ser Ile Arg Ile Leu Pro Glu His Glu Ile Lys
            20                  25                  30

Lys Thr Ala Thr Ser Phe Glu Gln Pro Ala Leu Leu Phe Ala Asn Pro
        35                  40                  45
```

```
Gln Asn Leu Tyr Glu Arg Arg Ala Lys Arg Leu Arg Lys Leu Ser Glu
    50                  55                  60

Ser His Pro Phe Ala Glu Tyr Leu Asn Phe Ala Ala Glu Val Ser Glu
65                  70                  75                  80

Val Gln Leu Lys Ile Leu Lys Met His Pro Leu Pro Gln Asp Glu Arg
                85                  90                  95

Leu Thr Lys Glu Asn Phe Ser Leu Asp Asn Ser Ile Gln Pro Leu His
                100                 105                 110

Thr Lys Asn Trp Lys Arg Asp Val Ile Trp Arg Glu Tyr Leu Ala Glu
            115                 120                 125

Ile Leu Ala Gln Ile Lys Leu Lys Ala Thr Asn Gln Ile Thr Thr Thr
        130                 135                 140

Ile Asp Trp Leu Glu Lys Ala Ser Asp Thr Glu Ile Glu Ser Leu Ala
145                 150                 155                 160

Asp Lys Leu Leu Ala Glu Asp Phe Ser Ser Val Ser Ser Asp Lys Ala
                165                 170                 175

Val Phe Ile Trp Ala Ala Leu Ser Leu Tyr Trp Leu Gln Leu Ala Gln
                180                 185                 190

Gln Ile Pro His Thr Thr Asn Met Glu Ser Gly Glu Asn Leu His Val
            195                 200                 205

Cys Pro Val Cys Asn Ala Ala Pro Val Ala Ser Val Val His Phe Gly
    210                 215                 220

Ala Ala Gln Gly Leu Arg Tyr Leu His Cys Ser Leu Cys Glu Ser Glu
225                 230                 235                 240

Trp Asn Met Val Arg Ala Lys Cys Ser Asn Cys Asn Gln Ala Glu His
                245                 250                 255

Leu Glu Tyr Trp Ser Ile Asp Glu Glu Met Ala Ala Val Arg Ser Glu
            260                 265                 270

Ser Cys Gly Asp Cys His Ser Tyr Leu Lys Ile Leu Phe Gln Glu Lys
        275                 280                 285

Asp Pro His Val Glu Pro Val Ala Asp Asp Leu Ala Thr Ile Tyr Leu
    290                 295                 300

Asp Ile Glu Met Glu Glu Lys Gly Phe Ala Arg Ser Gly Leu Asn Pro
305                 310                 315                 320

Phe Met Phe Pro Ser Glu Glu Ala
                325
```

GENE ENCODING FORMATE DEHYDROGENASES D & E AND METHOD FOR PREPARING SUCCINIC ACID USING THE SAME

BACKGROUND OF THE INVENTION

1. Field of the Invention

The present invention relates to novel genes encoding formate dehydrogenases D & E and to a method for preparing succinic acid using the same, more particularly, to formate dehydrogenases D & E converting formate to carbon dioxide and hydrogen, novel fdhD and fdhE genes encoding the formate dehydrogenases D & E, a recombinant vector containing the genes, a microorganism transformed with the recombinant vector, and a method for preparing succinic acid using the transformed microorganism.

2. Background of the Related Art

Succinic acid, which is a dicarboxylic acid ($HOOCCH_2CH_2COOH$) with four carbon atoms initially purified from amber resin, is used in a very wide range of industrial applications (Zeikus et al., *Appl. Microbiol. Biotechnol.*, 51:545, 1999). Particularly, as the utility of succinic acid as a main raw material of biodegradable polymers was recently proven, a rapid increase in the demand of succinic acid is expected (Willke et al., *Appl. Microbiol. Biotechnol.*, 66:131, 2004).

Succinic acid can be produced by chemical synthesis and fermentation. Most commercially available succinic acid recently has been produced from n-butane as a starting material derived from LNG or crude petroleum, by chemical manufacturers, such as BASF, DuPont and BP Chemicals. Chemical processes for the synthesis of succinic acid have the problem that they cause the discharge of large amounts of harmful solid wastes, waste solutions and waste gases (including carbon monoxide) during the preparation of succinic acid, and particularly, have the limitation that they use fossil raw material as a basic material. Only a small amount of succinic acid, which is used in special applications, such as medical drugs, is currently produced by traditional microbial processes.

In an attempt to solve the described problems occurring in the chemical processes for the synthesis of succinic acid, studies on the production of succinic acid by fermentation processes have been conducted by many researchers. The method for the production of succinic acid by fermentation is a method of producing succinic acid from renewable raw materials using microorganisms. Bacterial strains that are used in the production of succinic acid can be broadly divided into recombinant *E. coli* and ruminal bacteria, such as *Actinobacillus*, *Anaerobiospirillum*, *Bacteroides*, *Mannheimia*, *Succinimonas*, *Succinivibrio*, etc.

A research team of the University of Chicago has attempted to increase the production of succinic acid by preparing a mutant strain AFP111 (ATCC No. 202021) in which *E. coli* ldh and pfl genes involved in the production of lactic acid and formic acid have been removed and a ptsG gene of the glucose transfer system has been manipulated (U.S. Pat. No. 5,770,435).

Among ruminal bacteria, *Actinobacillus*, *Anaerobiospirillum* and *Mannheimia* strains have been relatively much-studied. Michigan Biotechnology Institute (MBI) has developed an *Actinobacillus succinogenes* 130Z strain (ATCC No. 55618) and a process for producing a high concentration of succinic acid using the same (U.S. Pat. No. 5,504,004). Also, such institute has developed *Anaerobiospirillum succiniciproducens* and its mutant strains, and a process for the production and purification of succinic acid (U.S. Pat. Nos. 5,521,075; 5,168,055; and 5,143,834).

However, the processes for preparing succinic acid using the described strains have low productivity and result in the production of large amounts of byproducts in addition to succinic acid, thus requiring high costs for the separation and purification of succinic acid. Accordingly, there has been an urgent need for the development of a bacterial system that has high productivity and at the same time, can inhibit the production of byproducts (Hong et al., *Biotechnol. Lett.*, 22:871, 2000).

For this purpose, the isolation of an excellent succinic acid-producing bacterial strain, the establishment of genome sequences and the understanding of metabolic characteristics of bacterial strains based on them are first required. With such basis, it then is necessary to secure gene manipulation technologies required for the construction of a novel gene recombinant bacterial strain. Although there has been a prior attempt to increase the production of succinic acid using the phosphoenolpyruvate carboxykinase (pcka) gene of *Anaerobiospirillum succiniciproducens* (Laivenieks et al., *Appl. Environ. Microbiol.*, 63:2273, 1997), the art has failed to develop a gene recombinant strain based on the full genome sequence of ruminal bacteria.

Meanwhile, the present inventors previously isolated a *Mannheimia succiniciproducens* MBEL55E strain from the rumen of a Korea cow that produces succinic acid in high efficiency using various substrates, and reported the full genome sequence of the strain (Hong et al., *Nature Biotechnol.*, 22:1275, 2004). Particularly, the above strain is characterized by immobilizing carbon dioxide, known as a greenhouse gas, in the synthesis of succinic acid. Also, this applicant previously prepared succinic acid with high yield by deleting a lactic acid dehydrogenase gene (ldhA) and a pyruvate formate-lyase (pfl) from *Mannheimia succiniciproducens* MBEL55E, so as to construct mutant strain *Mannheimia* sp. LPK (KCTC 10558BP), and deleting a phosphotransacetylase gene (pta), and an acetate kinase gene (acka) from the LPK strain to construct mutant strains *Mannheimia* sp. LPK7, and then culturing the resulting mutant strain in an anaerobic condition (WO 05/052135 A1). However, the mutant strain has a problem that it results in the accumulation of formate to a certain degree as a byproduct during the culture thereof.

Accordingly, there continues to be an urgent need in the art for the development of a bacterial system for high productivity, low byproduct succinic acid production that overcomes the deficiencies of the prior art.

SUMMARY OF THE INVENTION

The present invention relates to novel genes encoding formate dehydrogenases D & E derived from *Mannheimia succiniciproducens* MBEL55E that is usefully employed in the production of succinic acid.

The present invention relates on one aspect to a recombinant vector containing said gene, and a recombinant microorganism transformed with said recombinant vector.

Still another aspect of the present invention relates to a method for preparing succinic acid using said recombinant microorganism.

In one aspect, the present invention relates to formate dehydrogenases D & E having amino acid sequences of SEQ ID NOs: 7 and 8, respectively which have the activities of converting formate to carbon dioxide and hydrogen, as well as genes (fdhD and fdhE) encoding the formate dehydrogenases D & E. In one preferred aspect of the present invention, said genes preferably have DNA sequences of SEQ ID NOs: 5 and 6.

In another aspect, the present invention relates to a recombinant vector containing the fdhD and/or fdhE gene. In still another aspect, the present invention relates to a recombinant microorganism obtained by introducing the fdhD and/or fdhE gene or the recombinant vector into a host cell selected from the group consisting of bacteria, yeast and mold.

In a still further aspect of the present invention, the recombinant vector is preferably pMVDfdhDE, pMV19fdhDE, or pMExfdhDE, but is not limited thereto. Additionally, the host cell is a succinic acid-producing microorganism, a lactic acid-producing microorganism, or an ethanol-producing microorganism. The succinic acid-producing microorganism is the genus *Mannheimia* microorganism, and preferably, a *Mannheimia succiniciproducens* MBEL55E.

As shown in a succinate synthesis pathway described more fully hereinafter with reference to FIG. 1, the fdhD and fdhE genes can convert formate to $CO_2$ and $H_2$. Thus, it is possible to minimize formate which is produced as a byproduct in the production of succinic acid. Also, the reducing power (NADH) required for the synthesis of a succinate is conferred, as well as, produced $CO_2$ increases the production of succinic acid by promoting the conversion of pyruvate to malate and conversion of phosphoenolpyruvate to oxaloacetate, which is important in a succinate synthesis pathway.

Accordingly, the present invention relates in another aspect to a method for preparing succinic acid, the method including the steps of: culturing the recombinant microorganism; and recovering succinic acid from the culture broth of the recombinant microorganism. The steps of culturing the recombinant microorganism and recovering the succinic acid can be carried out by the culture method and the isolation and purification method of succinic acid, which are generally known in the prior fermentation industry.

The inventive fdhD and fdhE genes can decrease the accumulation of formate in the production of acetic acid, lactic acid or ethanol. Thus, when acetic acid-, lactic acid- or ethanol-producing microorganism is transformed with the genes according to the present invention, the production of formate as a byproduct can be reduced remarkably. Accordingly, the present invention provides a method for preparing acetic acid, lactic acid or ethanol, the method comprising the steps of: culturing the lactic acid- or ethanol-producing microorganism transformed with the fdhD and/or fdhE gene; and recovering acetic acid, lactic acid or ethanol from the microbial culture broth.

The above and other features and embodiments of the present invention will be more fully apparent from the following detailed description and appended claims.

DETAILED DESCRIPTION OF THE PREFERRED EMBODIMENT

The present invention is based on the discovery of a bacterial system for high productivity, low byproduct succinic acid production that overcomes the deficiencies of the prior art.

Figure 1:
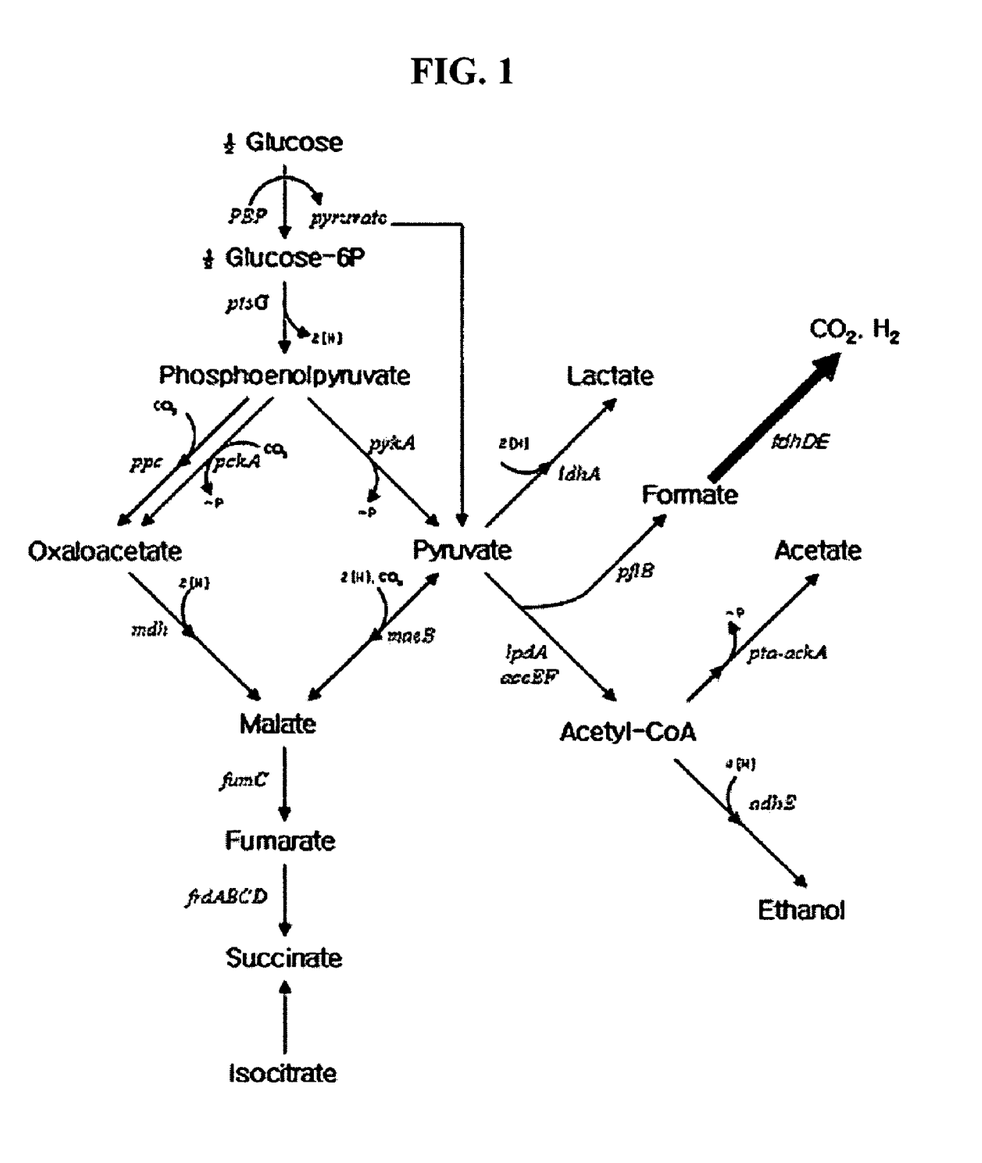
FIG. 1 is a schematic diagram showing a pathway for the synthesis of succinic acid from *Mannheimia* strain.

The present inventors have made extensive efforts to find the core gene involved in succinic acid metabolism in order to develop a microbial strain capable of minimizing the production of formate and of producing succinic acid with higher yield, on the basis of a succinic acid synthetic pathway shown in FIG. 1, and as a result, they have cloned formate dehydrogenase D & E-encoding genes (fdhD and fdhE) derived from *Mannheimia succiniciproducens* MBEL55E and determined the function thereof, thereby completing the present invention.

The present invention is more fully described hereinafter and with reference to illustrative examples. It is to be understood, however, that these examples are presented in order to more fully describe the present invention, and are correspondingly not intended to be construed to limit the present invention.

Although only the use of the specified expression vector and the genus *Mannheimia* microorganism, as a host cell, to express the inventive gene, is illustrated in the following examples, the use of other kinds of expression vectors and succinic acid-producing microorganisms will be readily apparent to those skilled in the art. Also, it will be readily apparent to a person skilled in the art that the known acetic acid-producing microorganism, lactic acid-producing microorganism and ethanol-producing microorganism in place of the succinic acid-producing microorganism can be used as a host cell.

EXAMPLE 1

Preparation of *Mannheimia/E. coli* Shuttle and Expression Vector pMEx

*Mannheimia/E. coli* shuttle vector pMEx was prepared from pMVSCS1 reported to be isolated from *Mannheimia* (Kehrenberg et al., *J. Antimicrob. Chemother.*, 49:383, 2002) and *E. coli* expression vector pKK223-3 (Amersham Pharmacia Biotech). For this purpose, pKK223-3 was partially digested with BamHI and AccI to collect a 2.7 kb fragment containing pBR322 ori and an ampicillin-resistant gene, and the single strand portions are filled with T4 DNA polymerase to make blunt ends. The blunt ends are ligated to prepare pKKD (2.7 kb). pMVSCS1 (5.6 kb) was digested with XhoII, and ligated with pKKD digested with restriction enzyme BamHI to prepare fusion vector pMVD (8.3 kb). The pMVD was digested with NcoI, and a 5.9 kb fragment was religated to construct *Mannheimia/E. coli* shuttle vector pME. The pME was digested with BamHI and ClaI, and a promoter and a transcription termination sequence of Mannheimia pckA gene (Hong et al., *Nature Biotechnol.*, 22:1275, 2004) were amplified to clone on the same restriction enzyme site whereby pMEx was constructed.

EXAMPLE 2

Identification of Novel Genes (fdhD and fdhE) Derived from *Mannheimia succiniciproducens* MBEL55E and Preparation of a Recombinant Plasmid Introduced with fdhDE Genes The fdhD and fdhE genes having SEQ ID NOs: 5 and 6, which encodes formate dehydragenase D & E derived from *Mirmheimia succiniciproducens* MBEL55E(KCTC 0769BP) were cloned, including a promoter and a transcription termination sequence, respectively.

Figure 2:
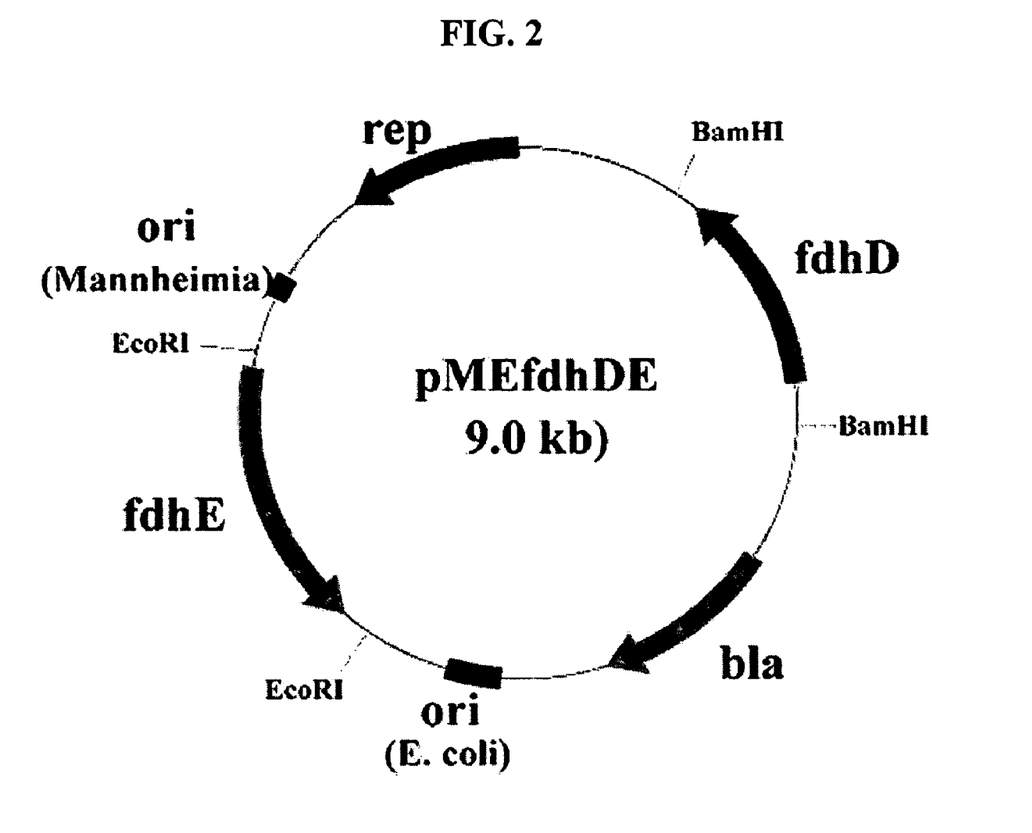
FIG. 2 is a gene map of recombinant plasmid pMExfdhDE.

For this purpose, the chromosome of *Mannheimia succiniciproducens* MBEL55E as a template was subjected to PCR with primers of SEQ ID NOs: 1 and 2 for fdhD and primers of SEQ ID NOs: 3 and 4 for fdhE under conditions shown in Table 1 below. The resulting fdhD andfdhE genes were amplified. fdhD was digested with restriction enzyme BamHI and ligated to *Mannheimia/E. coli* shuttle vector pMEx digested with the same restriction enzyme to construct plasmid pMExfdhD. The pMExfdhD was digested with EcoRi and ligated to fdhE digested with the same restriction enzyme to construct plasmid pMExfdhDE(FIG. 2). In this way, a formate dehydrogenase D & E-encoding genes (fdhD and fdhE) derived from *Mannheimia succiniciproducens* MBEL55E were cloned.

TABLE 1

Conditions for amplification of fdhD and fdhE genes.

| Gene | Primer | Restriction enzyme site contained in the primer | Reaction condition |
|---|---|---|---|
| fdhD | fdhD–F (SEQ ID NO: 1) fdhD–R (SEQ ID NO: 2) | BamHI | Cycle I: 94° C., 5 min Cycle II: (30 cycles) 94° C., 40 sec 56° C., 30 sec 72° C., 3 min Cycle III: 72° C., 5 min Cycle IV: 4° C., store |
| fdhE | fdhE–F (SEQ ID NO: 3), fdhE–R (SEQ ID NO: 4) | EcoRII | Cycle I: 94° C., 5 min Cycle II: (30 cycles) 94° C., 40 sec 56° C., 30 sec 72° C., 3 min Cycle III: 72° C., 5 min Cycle IV: 4° C., store |

The DNA sequences of the cloned fdhD and fdhE of *Mannheimia succiniciproducens* MBEL55E were analyzed and the amino acid sequences of formate dehydrogenases D & E were inferred. As a result, the fdhD and fdhE genes of *Mannheimia succiniciproducens* MBEL55E had DNA sequences of 846 bp (SEQ ID NO: 5) and 984 bp (SEQ ID NO: 6), and the formate dehydrogenases D & E consisted of 281 amino acid residues (SEQ ID NO: 7) and 328 amino acid residues (SEQ ID NO: 8), respectively.

The conserved domains of the fdhD and fdhE amino acid sequences derived from *Mannheimia succiniciproducens* MBEL55E were analyzed, and as a result, these genes showed high homology (fdhD score: 280, fdhE score: 376) with fdhD/NarQ family (gnl|CDD|3141, pfam02634) and fdhE (gnl|CDD|9775, pfam04216). The G+C amount of the *Mannheimia succiniciproducens* MBEL55EfdhD and fdhE were 42.0% and 40.8%, respectively.

Meanwhile, the frequency of using amino acid codons in the *Mannheimia succiniciproducens* MBEL55EfdhD and-fdhE genes were examined and the results are shown in Table 2 below. As shown in Table 2 below, the frequency of using amino acid codons in the fdhD and fdhE genes showed different result from that in generally known *E. coli*. For example, for the frequency of using lysine codons, AAAs were used at frequencies of 89% and 75% in the *Mannheimia succiniciproducens* MBEL55E fdhD and fdhE genes, respectively, but AAA was used at a frequency of 76% in generally known *E. coil*. For the frequency of using glutamate codons, GAAs were used at high frequencies of 82% and 88% in the *Mannheimia succiniciproducens* MBEL55E fdhD and fdhE genes, respectively, but GAA in *E. coli* was used at a frequency of 70%. Also, for the frequency of using glutamine codons, CAAs were used at high frequencies of 69% and 87% in the *Mannheimia succiniciproducens* MBEL55E fdhD and fdhE genes, respectively, but at a frequency of 31% in *E. coli*.

TABLE 2

Frequency of using amino acid codons

| Amino acid | Codon | Frequency of use in MBEL55E fdhD | Frequency of use in MBEL55E fdhE | Average frequency of use in E. coli |
|---|---|---|---|---|
| Ala | GCA | 0.27 | 0.27 | 0.22 |
|  | GCC | 0.14 | 0.17 | 0.25 |
|  | GCG | 0.50 | 0.33 | 0.34 |
|  | GCT | 0.09 | 0.23 | 0.19 |
| Arg | AGA | 0.31 | 0.00 | 0.04 |
|  | AGG | 0.00 | 0.00 | 0.03 |
|  | CGA | 0.13 | 0.38 | 0.05 |
|  | CGC | 0.25 | 0.31 | 0.37 |
|  | CGG | 0.13 | 0.08 | 0.08 |
|  | CGT | 0.19 | 0.23 | 0.42 |
| Asn | AAC | 0.43 | 0.14 | 0.61 |
|  | AAT | 0.57 | 0.86 | 0.39 |
| Asp | GAC | 0.23 | 0.14 | 0.41 |
|  | GAT | 0.77 | 0.86 | 0.59 |
| Cys | TGC | 0.38 | 0.44 | 0.57 |
|  | TGT | 0.63 | 0.56 | 0.43 |
| STOP | TAA | — | — | 0.62 |
|  | TAG | — | — | 0.09 |
|  | TGA | — | — | 0.30 |
| Gln | CAA | 0.69 | 0.87 | 0.31 |
|  | CAG | 0.31 | 0.13 | 0.69 |
| Glu | GAA | 0.82 | 0.88 | 0.70 |
|  | GAG | 0.18 | 0.13 | 0.30 |
| Gly | GGA | 0.14 | 0.25 | 0.09 |
|  | GGC | 0.29 | 0.25 | 0.40 |
|  | GGG | 0.19 | 0.00 | 0.13 |
|  | GGT | 0.38 | 0.50 | 0.38 |
| His | CAC | 0.00 | 0.18 | 0.48 |
|  | CAT | 1.00 | 0.82 | 0.52 |
| Ile | ATA | 0.29 | 0.20 | 0.07 |
|  | ATC | 0.18 | 0.20 | 0.46 |
|  | ATT | 0.53 | 0.60 | 0.47 |
| Leu | CTA | 0.06 | 0.06 | 0.03 |
|  | CTC | 0.03 | 0.06 | 0.10 |
|  | CTG | 0.06 | 0.11 | 0.55 |
|  | CTT | 0.10 | 0.33 | 0.10 |
|  | TTA | 0.48 | 0.31 | 0.11 |
|  | TTG | 0.26 | 0.14 | 0.11 |
| Lys | AAA | 0.89 | 0.75 | 0.76 |
|  | AAG | 0.11 | 0.25 | 0.24 |
| Met | ATG | 1.00 | 1.00 | 1.00 |
| Phe | TTC | 0.21 | 0.46 | 0.49 |
|  | TTT | 0.79 | 0.54 | 0.51 |
| Pro | CCA | 0.00 | 0.29 | 0.20 |
|  | CCC | 0.25 | 0.14 | 0.10 |
|  | CCG | 0.25 | 0.21 | 0.55 |
|  | CCT | 0.50 | 0.36 | 0.16 |
| Ser | AGC | 0.13 | 0.26 | 0.27 |
|  | AGT | 0.27 | 0.26 | 0.13 |
|  | TCA | 0.33 | 0.04 | 0.12 |
|  | TCC | 0.00 | 0.11 | 0.17 |
|  | TCG | 0.13 | 0.19 | 0.13 |
|  | TCT | 0.13 | 0.15 | 0.19 |
| Thr | ACA | 0.25 | 0.50 | 0.12 |
|  | ACC | 0.21 | 0.14 | 0.43 |
|  | ACG | 0.33 | 0.07 | 0.23 |
|  | ACT | 0.21 | 0.29 | 0.21 |
| Trp | TGG | 1.00 | 1.00 | 1.00 |
| Tyr | TAC | 0.50 | 0.33 | 0.47 |
|  | TAT | 0.50 | 0.67 | 0.53 |
| Val | GTA | 0.24 | 0.36 | 0.17 |
|  | GTC | 0.10 | 0.07 | 0.20 |
|  | GTG | 0.38 | 0.14 | 0.34 |
|  | GTT | 0.29 | 0.43 | 0.29 |

EXAMPLE 3

Production of Succinic Acid by Use of Transformed *Mannheimia*

The recombinant plasmid pMExfdhDE constructed in Example 2 was transformed into *Mannheimia succiniciproducens* MBEL55E by electroporation to prepare MBEL55EpMExfdhDE. Also, pMEx was introduced into *Mannheimia succiniciproducens* MBEL55E, to prepare MBEL55EpMEx.

Each of the prepared recombinant strains was inoculated in 10 ml of a complex medium containing 9 g/l of glucose and cultured in an anaerobic condition at 39° C. for 16 hours. Each of the cultured strains was transferred in 250 ml of a complex medium containing 9 g/l of glucose and further cultured in the medium at 39° C. At this time, 100 µg/l of ampicillin as an antibiotic was added. The fermentation of each of the strains was performed by inoculating 250 ml of the *Mannheimia* culture broth in 2.5 L of a complex medium, and the fermentation conditions were as follows: initial glucose concentration: 20 g/l, pH: 6.8, and culture temperature: 39° C. For the adjustment of pH during the fermentation, ammonia solution (28%, v/v) was used, and the concentration of antibiotic ampicillin was the same as described above. A sample from each of the recombinant *Mannheimia* strains was collected during the fermentation, and the collected sample was centrifuged at 13,000 rpm and 4° C. for 10 minutes, and the concentrations of metabolites and succinic acid in the supernatant were analyzed by high-performance liquid chromatography (HPLC). The results are shown in Table 3 below.

As shown in Table 3, in the case where the recombinant plasmid pMExfdhDE containing the fdhD and fdhE genes was introduced into the *Mannheimia succiniciproducens* MBEL55E, the concentration of formate was reduced. These results suggest that the fdhD and fdhE genes encode an enzyme conferring an important reduction power on the step of producing succinic acid from fumarate in the succinic acid-producing pathway by synthesis of NADH.

minutes. The precipitated cells were washed 2 times with an iced buffer solution (100 mM Tris-HCl (pH 7.0), 20 mM KCl, 5 mM $MnSO_4$, 2 mM DTT, 0.1 mM EDTA), and the washed cells were suspended in the same buffer and the cell membranes were disrupted by sonication. The cell debris was removed by a centrifugation, and the cell extract supernatant was used for the measurement of enzyme activities.

The enzyme activity of the cell extracts was measured with a spectrophotometer, in which the cell extract was allowed to react by adding a reaction buffer (200 mM sodium formate, 2 mM NAD+ and 100 mM potassium phosphate buffer, pH 6.5) to a 1 cm-width cuvette and adding the cell extract to the reaction buffer to a final volume of 1 ml, and the NADH at 340 nm was measured. The results are shown in Table 4.

As shown in Table 4, the MBEL55EpMExfdhDE cell extract showed 305% increase in enzyme activity compared to the MBEL55EpMEx cell extract. This result confirms that the fdhD and fdhE genes according to the present invention are genes encoding formate dehydrogenases D & E having the activity of converting formate to carbon dioxide and hydrogen.

TABLE 4

Enzyme activities of transformed *Mannheimia* strains

| Strain | Plasmid | *Enzyme activity (U) | Enzyme activity increase (%) |
|---|---|---|---|
| MBEL55E | pMEx | 3.6 | 100 |
| MBEL55E | pMExfdhDE | 11.0 | 305 |

*Enzyme activity shows the titer of formate dehydrogenase contained in 1 mg of total protein. An enzyme activity of 1.0 U is defined as the amount of enzyme required for converting 1 nmole of a substrate to a certain product at 37° C. for 1 minute.

In the measurement of enzyme activity according to the present invention, it was identified that the reduction of

TABLE 3

Productions of succinic acid using transformed *Mannheimia*

| Strain | Plasmid | Fermentation time (hrs.) | Cell concentration ($OD_{600}$) | Formate concentration (g/l) | Formate reduction rate (%) | Succinic acid concentration (g/l) |
|---|---|---|---|---|---|---|
| MBEL55E | pMEx | 8 | 7.2 | 4.66 | 100 | 10.4 |
| MBEL55E | pMExfdhDE | 10 | 6.5 | 2.03 | 156 | 9.4 |

Figure 3:
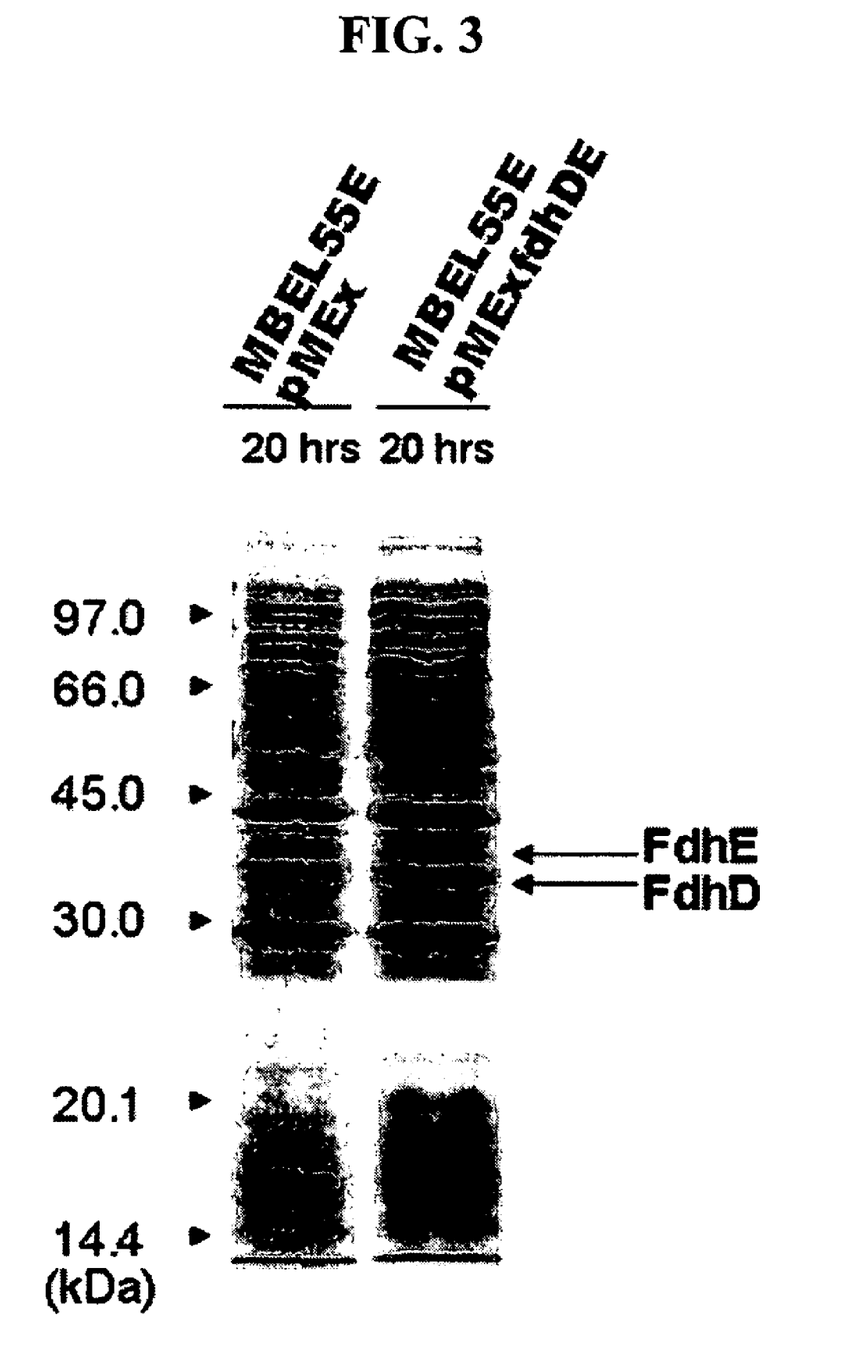
FIG. 3 is an SDS-PAGE showing the protein expression of recombinant *Mannheimia* MBEL55EpMExfdhDE containing recombinant plasmid pMExfdhDE.

Meanwhile, each of the strains was analyzed by SDS-PAGE, and the results are shown in FIG. 3. As can be seen in FIG. 3, the recombinant *Mannheimia succiniciproducens* MBEL55EpMExfdhDE transformed with the recombinant plasmid pMExfdhDE showed a remarkable increase in the expression of formate dehydrogenases D & E as compared to the recombinant *Mannheimia succiniciproducens* MBEL55EpMEx(control group) transformed with pMEx.

EXAMPLE 4

Measurement of Formate Dehydrogenase D & E Activities

The culture broth of the recombinant *Mannheimia succiniciproducens* MBEL55EpMExfdhDE prepared in Example 3 was centrifuged at 13,000 rpm and 4° C. for 5

NAD+ produced NADH and carbon dioxide. Thus, the formate dehydrogenases D & E confer to reducing power (NADH) required for the synthesis of a succinate, moreover $CO_2$ produced from the formate dehydrogenases D & E is useful in the conversion of pyruvate to malate and conversion of phosphoenolpyruvate to oxaloacetate, which is important in a succinate synthesis pathway.

The activity of the formate dehydrogenases according to the present invention was compared to the known enzyme, and the result is shown in Table 5 below. As shown in Table 5, the formate dehydrogenases of the *Mannheimia* strain transformed with the inventive fdhD and fdhE genes showed much higher activity than the formate dehydrogenase of *E. coli* K12(Gray et al., *Biochim. Biophys. Acta*, 117:33, 1966).

TABLE 5

Comparison of formate dehydrogenase activity between transformed *Mannheimia* and *E. coli*

| Strain | Enzyme activity (U) | Gene homology (%) |
|---|---|---|
| MBEL55EpMExfdhDE | 11 | 60.1 (fdhD) 57.0 (fdhE) |
| *E. coli* K12 | 5 | |

As described and proven in detail above, the present invention provides the novel genes (fdhD and fdhE) encoding the formate dehydrogenases D & E. The nucleotide sequences of the fdhD and fdhE genes may be DNA sequences of SEQ ID NO: 5 and SEQ ID NO: 6, respectively, or sequences having appropriate homology thereto (e.g., that is at least 85%, and more preferably is at least 90, 91, 92, 93, 94, 95, 96, 97, 98, or 99% homologous to the nucleotide sequences of SEQ ID NO: 5 and SEQ ID NO: 6).

The novel genes according to the present invention are useful to prepare a recombinant microorganism capable of effectively reducing formate which is produced as a byproduct in the production of succinic acid, as well as conferring reducing power (NADH) required for the synthesis of succinic acid. The fdhD and fdhE genes are also useful to prepare a recombinant microorganism for minimizing the production of formate as a byproduct, during the preparation of acetic acid, lactic acid or ethanol. Accordingly, the fdhD and fdhE genes according to the present invention will be useful in increasing the productivity of various metabolites in the operation of central metabolic pathways by the combination with a suitable metabolic pathway.

While the present invention has been described in detail with reference to specific features, it will be apparent to those skilled in the art that this description is illustrative only of a preferred embodiment and is not intended in any way to limit the scope of the present invention, as defined by the appended claims and equivalents thereof.

---

The invention claimed is:

1. An isolated fdhD gene encoding a formate dehydrogenase D having an amino acid sequence of SEQ ID NO: 7.

2. The isolated fdhD gene of claim 1, which has a DNA sequence of SEQ ID NO: 5.

3. An isolated fdhE gene encoding a formate dehydrogenase E having an amino acid sequence of SEQ ID NO: 8.

4. The isolated fdhE gene of claim 3, which has a DNA sequence of SEQ ID NO: 6

5. A recombinant vector containing at least one of (i) an isolated fdhD gene having the DNA sequence of SEQ ID NO: 5 which encodes a protein having formate dehydrogenase D activity and (ii) an isolated fdhE gene having the DNA sequence of SEQ ID NO: 6 which encodes a protein having formate dehydrogenase E activity.

6. The recombinant vector of claim 5, which is pMExfdhDE.

7. A recombinant microorganism obtained by introducing a recombinant vector into a host cell selected from the group consisting of bacteria, yeast and mold, wherein said recombinant vector is selected from the group consisting of:

(i) a recombinant vector containing at least one of (a) an isolated fdhD gene having the DNA sequence of SEQ ID NO: 5 which encodes a protein having formate dehydrogenase D activity and (b) an isolated fdhE gene having the DNA sequence of SEQ ID NO: 6 which encodes a protein having formate dehydrogenase E activity; and (ii) pMExfdhDE.

8. The recombinant microorganism of claim 7, wherein the host cell is a succinic acid-producing microorganism.

9. The recombinant microorganism of claim 8, wherein the succinic acid-producing microorganism is of the genus *Mannheimia*.

10. The recombinant microorganism of claim 9, wherein the succinic acid-producing microorganism is *Mannheimia succiniciproducens* MBEL55E.

11. The recombinant microorganism of claim 7, wherein the host cell is a acetic acid-producing microorganism.

12. The recombinant microorganism of claim 7, wherein the host cell is a lactic acid-producing microorganism.

13. The recombinant microorganism of claim 7, wherein the host cell is an ethanol-producing microorganism.

14. A method for preparing succinic acid, the method comprising the steps of: culturing the recombinant microorganism of claim 8; and recovering succinic acid from the culture broth of the recombinant microorganism.

15. The recombinant microorganism of claim 7, wherein the recombinant microorganism is a succinic acid-producing microorganism.

* * * * *

UNITED STATES PATENT AND TRADEMARK OFFICE
CERTIFICATE OF CORRECTION

PATENT NO. : 7,241,594 B2
APPLICATION NO. : 11/228945
DATED : July 10, 2007
INVENTOR(S) : Sang Yup Lee et al.

It is certified that error appears in the above-identified patent and that said Letters Patent is hereby corrected as shown below:

Column 5, line 3: "andfdhE" should be -- and fdhE --.

Column 5, line 8: "EcoRi" should be -- EcoRI --.

Column 5, line 49: "MBEL55EfdhD" should be -- MBEL55E fdhD --.

Column 5, line 53: "MBEL55EfdhD" should be -- MBEL55E fdhD --.

Signed and Sealed this

Twenty-third Day of October, 2007

JON W. DUDAS
*Director of the United States Patent and Trademark Office*